United States Patent
Olivier-Bourbigou et al.

(10) Patent No.: US 9,556,296 B2
(45) Date of Patent: Jan. 31, 2017

(54) PROCESS FOR METATHESIS OF OLEFINS OBTAINED FROM FISCHER-TROPSCH FRACTIONS USING A RUTHENIUM COMPLEX COMPRISING A DISSYMMETRICAL N-HETEROCYCLIC DIAMINOCARBENE

(71) Applicants: CENTRE NATIONAL DE LA RECHERCHE SCIENTIFIQUE, Paris (FR); ECOLE NATIONALE SUPERIEURE DE CHIMIE DE RENNES, Rennes (FR); IFP ENERGIES NOUVELLES, Rueil-Malmaison (FR)

(72) Inventors: Helene Olivier-Bourbigou, Saint Genis-Laval (FR); Francois Hugues, Vernaison (FR); Severine Forget, Bourgoin-Jallieu (FR); Mathieu Rouen, La Bouexiere (FR); Marc Mauduit, Vitre (FR)

(73) Assignees: CENTRE NATIONAL DE LA RECHERCHE SCIENTIFIQUE, Paris (FR); IFP ENERGIES NOUVELLES, Rueil-Malmaison (FR); ECOLE NATIONALE SUPERIEURE DE CHIMIE DE RENNES, Rennes (FR)

( * ) Notice: Subject to any disclaimer, the term of this patent is extended or adjusted under 35 U.S.C. 154(b) by 79 days.

(21) Appl. No.: 14/261,555

(22) Filed: Apr. 25, 2014

(65) Prior Publication Data

US 2014/0323671 A1    Oct. 30, 2014

(30) Foreign Application Priority Data

Apr. 26, 2013 (FR) ..................... 13 53830

(51) Int. Cl.
*C08F 210/14* (2006.01)
*C07F 15/00* (2006.01)
*C07C 6/04* (2006.01)
*C10G 29/20* (2006.01)

(52) U.S. Cl.
CPC ............ *C08F 210/14* (2013.01); *C07C 6/04* (2013.01); *C07F 15/0046* (2013.01); *C10G 29/205* (2013.01); *C07C 2531/22* (2013.01); *C07C 2531/24* (2013.01); *C10G 2300/1088* (2013.01); *C10G 2300/1092* (2013.01); *C10G 2300/70* (2013.01); *C10G 2400/20* (2013.01); *C10G 2400/22* (2013.01)

(58) Field of Classification Search
CPC ...... C07F 15/00; C07D 233/06; C07D 213/02; C07D 233/02; C07C 6/02; C07C 67/333; C07C 67/343
See application file for complete search history.

(56) References Cited

U.S. PATENT DOCUMENTS

2003/0135080 A1   7/2003 Botha et al.
2006/0211905 A1*  9/2006 Forman et al. ............... 585/645
2011/0306585 A1* 12/2011 Youngs et al. ............... 514/186

FOREIGN PATENT DOCUMENTS

WO    01/46096 A1    6/2001
WO    2013/079820 A1  6/2013

OTHER PUBLICATIONS

French Search Report dated Jan. 8, 2014 issued in corresponding FR 1353830 application (pp. 1-2).

* cited by examiner

*Primary Examiner* — Robert Harlan
(74) *Attorney, Agent, or Firm* — Millen White Zelano and Branigan, PC; Csaba Henter; Anthony Zelano

(57) ABSTRACT

This invention describes a process for metathesis of olefins from feedstocks obtained from the Fischer-Tropsch process, using as catalyst a ruthenium alkylidene complex comprising a saturated or unsaturated, dissymmetrical N-heterocyclic carbene (NHC) ligand.

21 Claims, No Drawings

PROCESS FOR METATHESIS OF OLEFINS OBTAINED FROM FISCHER-TROPSCH FRACTIONS USING A RUTHENIUM COMPLEX COMPRISING A DISSYMMETRICAL N-HETEROCYCLIC DIAMINOCARBENE

FIELD OF THE INVENTION

This invention relates to the metathesis of olefins obtained from Fischer-Tropsch feedstocks, which is a catalytic reaction for transformation of identical or different olefins consisting in exchanging the alkylidene groups of the starting olefins to form new olefins.

TERMINOLOGY

Hereinafter, "cycloalkyl" is defined as any cyclic secondary aliphatic alkyl group.

"Aryl" refers to an aromatic group.

N-Heterocyclic diaminocarbenes or NHC-heterocyclic carbenes (N-heterocyclic carbene in English) are defined as ligands of the imidazolidine-2-ylidene (saturated heterocyclic NHC) type and ligands of the imidazoline-2-ylidene (unsaturated heterocyclic NHC) type.

Dissymmetrical N-heterocyclic diaminocarbenes are defined as N-heterocyclic diaminocarbenes that carry non-identical carbon-containing groups on the nitrogen atoms.

PRIOR ART

The metathesis reaction has become an important tool for forming carbon-carbon bonds. It is implemented in the fields of petrochemistry, polymers, oleochemistry, and fine chemistry. The isolated carbenic complexes based on ruthenium have been described for catalyzing this reaction (Chem. Rev. 2010, 110, 1746-1787).

The patent WO2011/056874 describes a catalytic composition based on a ruthenium complex comprising an N-heterocyclic carbene with 5 members of the saturated dissymmetrical NHC type for the production of alpha-olefins by metathesis of triglycerides or fatty acids, for example for the production of decene-1 by reaction of methyl oleate with ethylene.

The patent WO2007/075427 describes a ruthenium complex that carries an N-heterocyclic carbene with 5 NHC-type members in which one of the nitrogen atoms is substituted by a phenyl group that contains hydrogen in the ortho position and that is substituted in the prime ortho position. These complexes are used for catalyzing the metathesis of olefins by the closing of a cycle.

The ruthenium (Ru) complexes comprising an N-heterocyclic diaminocarbene ligand with 5 dissymmetrical NHC-type members, i.e., carrying non-identical carbon-containing groups, have been described by Blechert (Organometallics, 2006, 25, 25-28 and Dalton Trans. 2012, 41, 8215-8225). A wide variety of ruthenium-based catalysts is described, but each of these catalysts is designed to be applied to a very specific metathesis reaction. Their transposition to another metathesis reaction is not obvious.

Relative to the dissymetrical diaminocarbenic ligands (unsaturated or saturated NHC), the nature and the selection of the substituent carbon-containing groups remain very limited.

For example, for unsaturated NHC, this is due in particular to the difficulty of the synthesis of precursor dissymmetrical imidazolium salts. Actually, for synthesizing a dissymmetrical 1,3-disubstituted imidazoline-2-ylidene diaminocarbenic ligand, it is crucial first to generate a precursor imidazolium salt. This synthesis is complex and calls for either a very high number of chemical operations (4 to 6 separate chemical operations) or a limited preliminary selection of substituent carbon-containing groups.

Furthermore, the parasitic isomerization of the double bond of olefins of the feedstock or products of metathesis very often leads to the formation of undesirable by-products and appears to be a limitation to the economical development of these catalytic systems. The isomerization of the double bond is reflected by a drop in selectivity of desired linear internal olefins.

The patent WO01/46096 describes a process of metathesis for converting short C4-C10 olefins that are primarily alpha-olefins and whose optional branching is positioned with at least 2 carbon atoms of the double bond, able to be derived from a Fischer-Tropsch process, into longer C8-C18 olefins by using homogeneous complexes, primarily based on the Grubbs-type ruthenium ($1^{st}$ generation) of the formula $RuCl_2(PCy_3)_2(CHPh)$ with an improved selectivity relative to the heterogeneous catalysts that are known to one skilled in the art. In this patent, the effect of poisons of certain oxidized compounds contained in the Fischer-Tropsch feedstocks on their conversion by metathesis catalyzed by the Grubbs complex is also described.

It is known that the oxidized derivatives change the behavior of metathesis catalysts (see the review A. by Klerk Green Chem. 2008, Vol. 10, No. 12, pp. 1237-1344).

Surprisingly enough, it was found that the use of a catalyst with ruthenium alkylidene comprising a saturated or unsaturated dissymmetrical N-heterocyclic carbenic (NHC) ligand made it possible to solve the problems mentioned above and to obtain an activity and a selectivity for the metathesis reaction that are maintained and even improved, with olefinic feedstocks originating from a Fischer-Tropsch process and having 3 to 10 carbon atoms.

The process according to the invention makes it possible to obtain olefins with good selectivity for the internal linear olefins while limiting the production of olefins having a wide distribution of carbon atoms.

Another advantage of the invention is to improve the selectivity of the reaction for metathesis of the feedstocks obtained from the Fischer-Tropsch process in such a way as to optimize the desired olefin yield, which has the result of optimizing the separation of products and also of improving the overall economy of the process.

The process according to the invention also makes it possible to obtain a good conversion of the olefins to be transformed that are contained in the feedstocks obtained from the Fischer-Tropsch process, and this is done with very small concentrations of ruthenium.

DETAILED DESCRIPTION OF THE INVENTION

The invention relates to a process for metathesis of feedstocks obtained from the Fischer-Tropsch process using as catalyst a ruthenium alkylidene complex of Formula (I) or (II)

Formula I

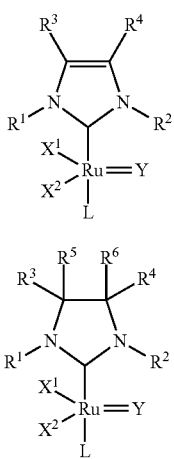

Formula II

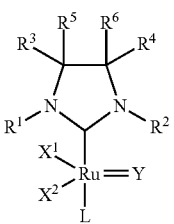

in which:
R$^1$ is an aryl group,
R$^2$ is a cycloalkyl group,
X$^1$ and X$^2$ are identical or different, and X$^1$ and X$^2$ are anionic ligands,
L is a ligand that is an electron donor and uncharged,
Y represents an alkylidene fragment, for example indenylidene, which may or may not be substituted, or else Y forms a styrenylidene ether with L,
R$^3$, R$^4$, R$^5$, and R$^6$—identical or different—are hydrogen, halide, alkyl, cycloalkyl, aryl or arylalkyl groups, each being able to be substituted by alkyl, halide, or alkoxy groups or by a phenyl group that is optionally substituted by halide, alkyl, or alkoxy groups,
and in which the cycloalkyl group is a cyclic secondary aliphatic alkyl.

The Catalyst

The catalyst that is used in the process according to the invention is a saturated or unsaturated, dissymmetrical N-heterocyclic carbenic (NHC) complex that is based on ruthenium.

The catalyst that is used in the process of the invention is a ruthenium alkylidene complex corresponding to Formula (I) or (II) in which the cycloalkyl group is a cyclic secondary aliphatic alkyl Formula I

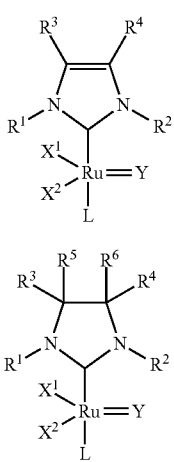

Formula II

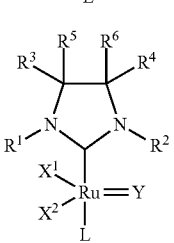

with
R$^1$ is an aryl group,
R$^2$ is a cycloalkyl group,
X$^1$ and X$^2$ are identical or different, and X$^1$ and X$^2$ are anionic ligands,
L is a ligand that is an electron donor and uncharged,
Y represents an alkylidene fragment, for example indenylidene, which may or may not be substituted, or else Y forms a styrenylidene ether with L,
R$^3$, R$^4$, R$^5$, and R$^6$—identical or different—are hydrogen, halide, alkyl, cycloalkyl, aryl or arylalkyl groups, each being able to be substituted by alkyl, halide, or alkoxy groups or by a phenyl group that is optionally substituted by halide, alkyl, or alkoxy groups.

The ruthenium complex according to the invention of Formula (I) or Formula (II) comprises at least one unsaturated or saturated, dissymmetrical N-heterocyclic diaminocarbene for which one of the nitrogen atoms carries an R$^1$ aryl group and the other nitrogen atom carries an R$^2$ cycloalkyl group.

R$^1$ is an aryl group.

"Aryl" is defined as an aromatic group, for example an aromatic monocyclic or polycyclic group, preferably monocyclic or bicyclic, having a number of carbon atoms of between 6 and 20. Preferred aryl groups are advantageously selected from among the phenyl, naphthyl, and mesityl groups. When the group is polycyclic, i.e., it comprises more than a cyclic core, the cyclic cores can advantageously be condensed two by two or attached two by two by σ bonds. R$^1$ can be an aromatic monocyclic or polycyclic group that has a number of carbon atoms of between 6 and 20.

In terms of this invention, R$^2$ is a cycloalkyl group.

"Cycloalkyl" is defined as a cyclic secondary aliphatic alkyl group, for example a monocyclic hydrocarbon-containing group that has a number of carbon atoms that is greater than 2, preferably between 3 and 24, in a more preferred manner between 4 and 12, preferably a cyclopentyl, cyclohexyl, cyclooctyl or cyclododecyl group or a polycyclic (bicyclic or tricyclic) group that has a number of carbon atoms that is greater than 2, preferably between 3 and 18, such as, for example, the adamantyl or norbornyl groups. R$^2$ can be a monocyclic cycloalkyl group that has a carbon number of between 3 and 24 or a polycyclic group that has a carbon number of between 3 and 18.

In terms of this invention, the substituents R$^3$, R$^4$, R$^5$, and R$^6$—identical or different—are selected from the group that consists of a hydrogen atom, halides, or alkyl, cycloalkyl, aryl or arylalkyl groups, each being able to be substituted by alkyl, halide, or alkoxy groups or by a phenyl group that is optionally substituted by halide, alkyl, or alkoxy groups.

For R$^3$, R$^4$, R$^5$, and R$^6$, "alkyl" is defined as a linear or branched hydrocarbon-containing chain that has 1 to 15 carbon atoms, preferably 1 to 10, and even more preferably 1 to 4, carbon atoms. Preferred alkyl groups are advantageously selected from among the methyl, ethyl, propyl, isopropyl, butyl, isobutyl, and tert-butyl groups.

For R$^3$, R$^4$, R$^5$, and R$^6$, an "alkoxy" substituent is defined as an alkyl-O— group in which the term alkyl has the meaning provided above. Preferred examples of alkoxy substituents are the methoxy or ethoxy groups.

For R$^3$, R$^4$, R$^5$, and R$^6$, "cycloalkyl" is defined as a cyclic or monocyclic hydrocarbon-containing group that preferably has 3 to 10 carbon atoms, in particular a cyclopentyl or cyclohexyl group, or a polycyclic (bicyclic or tricyclic) group that has 4 to 18 carbon atoms, in particular adamantyl or norbornyl.

For $R^3$, $R^4$, $R^5$, and $R^6$, "aryl" is defined as an aromatic monocyclic or polycyclic group—preferably a monocyclic or bicyclic group—that has 6 to 20 carbon atoms, preferably phenyl or naphthyl. When the group is polycyclic, i.e., it comprises more than one cyclic core, the cyclic cores can be condensed two by two or attached two by two by σ bonds.

For $R^3$, $R^4$, $R^5$, and $R^6$, "arylalkyl" or "aralkyl" is defined as a linear or branched hydrocarbon-containing group that carries a monocyclic aromatic cycle that has 7 to 12 carbon atoms, with the aliphatic chain comprising 1 or 2 carbon atoms. A preferred arylalkyl or aralkyl group is the benzyl group.

$R^3$, $R^4$, $R^5$, and $R^6$ can be identical or different and can be selected from among:

A hydrogen atom,
A halide,
A linear or branched alkyl group that has 1 to 15 carbon atoms,
A monocyclic cycloalkyl group that has 3 to 10 carbon atoms, or a polycyclic cycloalkyl group that has 4 to 18 carbon atoms,
An aromatic monocyclic or bicyclic aryl group that has 6 to 20 carbon atoms,
A linear or branched arylalkyl group that carries a monocyclic aromatic cycle that has 7 to 12 carbon atoms, with the aliphatic chain comprising 1 or 2 carbon atoms.

The Ligands $X^1$ and $X^2$ $X^1$ or $X^2$ is an anionic ligand that can be selected from among halides, sulfates, alkyl sulfates, aryl sulfates, alkyl sulfonates, aryl sulfonates, alkyl sulfinates, aryl sulfinates, acyls, carbonates, carboxylates, alcoholates, phenolates, amides, and pyrolides, which may or may not be substituted by one or more groups selected from among the alkyl groups that have 1 to 12 carbon atoms, the alcoholate groups that have 1 to 12 carbon atoms, the aryl groups that have 5 to 24 carbon atoms, and the halides, said substituent groups, except for halides, themselves being substituted or not by one or more of the groups that are selected from among the halides, the alkyl groups that have 1 to 6 carbon atoms, the alcoholate groups that have 1 to 6 carbon atoms, and the aryl groups.

Preferably, $X^1$ or $X^2$ is selected from among the halide ligands, the benzoates, the tosylates, the mesylates, the trifluoromethane-sulfonates, the pyrolides, the $CF_3CO_2$ trifluoroacetate groups, the $CH_3CO_2$ acetates, the alcoholates, and the phenolates.

In a preferred manner, the anionic ligands $X^1$ or $X^2$ are selected from among the halide ligands, and in a very preferred manner, the ligands $X^1$ and $X^2$ are identical and are chlorides or bromides.

The Ligand L

According to the invention, L is an uncharged electron-donor ligand.

In one embodiment, the group Y and the ligand L can be combined within the same chemical entity of the styrenylidene ether type.

In one embodiment, L is a phosphorated ligand of formula $PR'_3$, in which P is a phosphorus atom and R' is selected from among the groups R and (OR), in which the groups R are identical or different and are selected from among the following groups: hydrogen, halides, alkyls, cycloalkyls, aryls, and arylalkyls, which may or may not be substituted, each of the groups comprising up to 20 carbon atoms, and the substituents of said groups can advantageously be selected from among the halides, the alkyl groups, and the aryl groups that have up to 20 carbon atoms; the ligand L can be a dissymmetrical, saturated or unsaturated, N-heterocyclic diaminocarbene.

The phosphorated ligand L of the ruthenium compound is preferably a phosphine, in a preferred manner a trialkylphosphine or a tricycloalkylphosphine that is selected from among tricyclohexylphosphine, triisopropylphosphine, and tricyclopentylphosphine; a dialkylphosphine or a dicycloalkylphosphine that is selected from among dicyclohexylphosphine, dicyclohexylphenylphosphine, di-tert-butylphosphine, and di-tert-butylchlorophosphine or a triarylphosphine that is selected from among triphenylphosphine, tri(methylphenyl)phosphine, trimesitylphosphine, tri(dimethylphenyl)phosphine, and tri[(trifluoromethyl)phenyl]phosphine.

In a preferred manner, $X^1$ and $X^2$ are identical and are selected from among the chloride or bromide ligands; L is a tricyclohexylphosphine, and Y is an indenylidene group that may or may not be substituted.

In a preferred manner, the catalyst that is used in this invention corresponds to the following formulas:

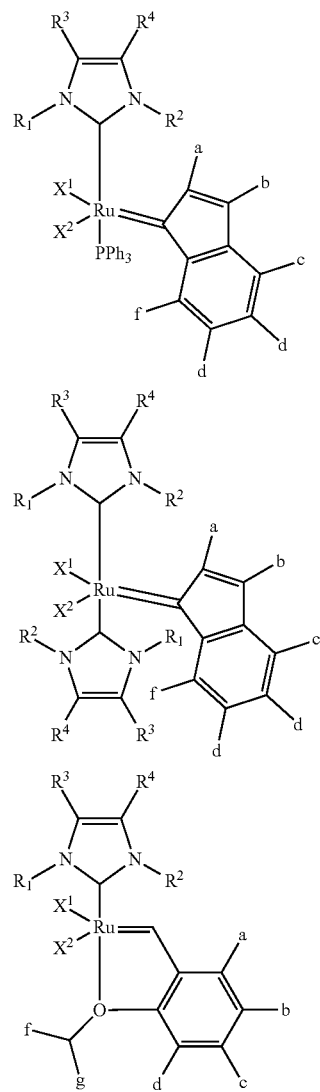

-continued

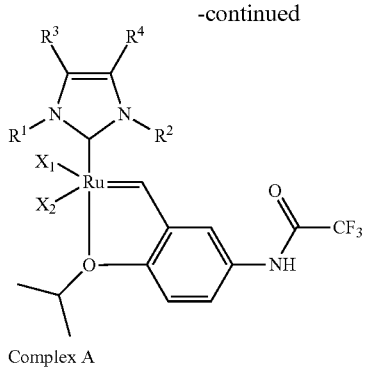

Complex A

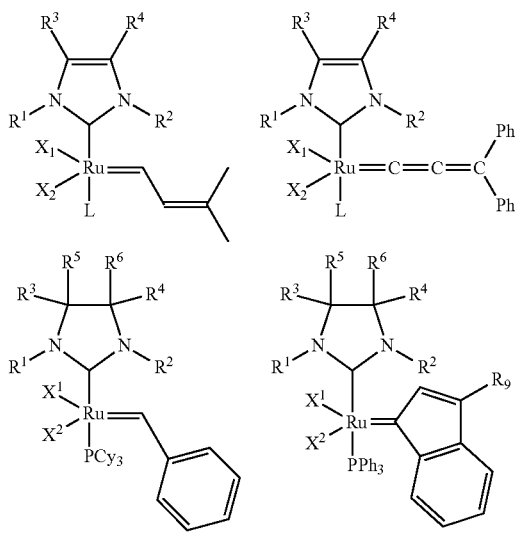

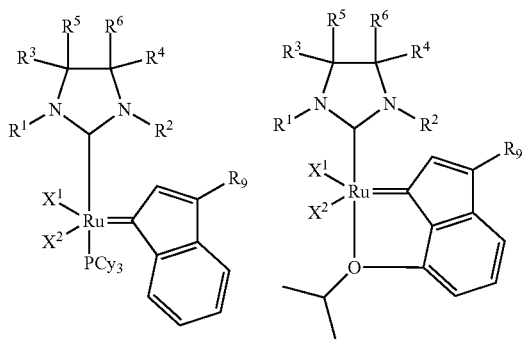

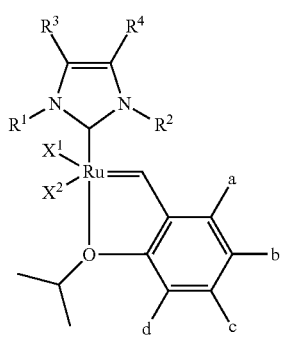

-continued

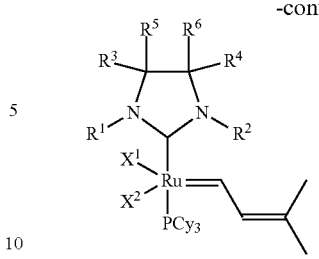

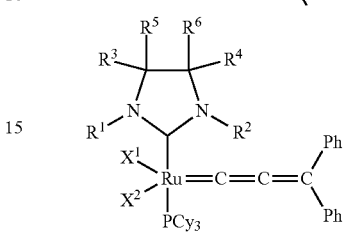

in which:

$X^1$ and $X^2$, identical or different, are as defined above, and preferably selected from among the chloride and bromide ligands, $R^3$, $R^4$, $R^5$, and $R^6$ are defined as for Formulas (I) and (II), and are preferably a hydrogen atom, $R^1$, defined as for Formulas (I) and (II), is preferably selected from the group that consists of 2,4,6-trimethylphenyl, 2,6-di-iso-propylphenyl, 3,5-dinitrophenyl, 2,4,6-tris(trifluoromethyl)phenyl, 2,4,6-trichlorophenyl, and hexafluorophenyl, $R^2$, defined as in Formulas (I) and (II), is preferably selected from the group that consists of cyclopentyl, cyclohexyl, cycloheptyl, cyclooctyl, cyclodecyl, cyclododecyl, and cyclopentadecyl, a, b, c, d, e, and f are selected independently of one another in the group that consists of a hydrogen atom, an alkyl group, and a heteroalkyl group. In the complex A, f and g can optionally form a cycle, $R^9$ can be a hydrogen or an aryl group that may or may not be substituted. In a preferred manner, $R^9$ is a phenyl group that may or may not be substituted.

Preferably, the ligands $X^1$ and $X^2$ are identical and are selected from among the chloride or bromide ligands.

In a preferred manner, L is a tricyclohexylphosphine, and Y is an indenylidene group, which may or may not be substituted.

The Feedstock

The feedstocks that are obtained from the Fischer-Tropsch process are advantageously selected from among the light fractions, i.e., the fractions that contain linear light olefins and even more advantageously linear alpha-olefins that have 3 to 10 carbon atoms.

The feedstocks according to the invention can contain branched olefins and internal olefins. They can also contain alkanes.

The feedstocks according to the invention can contain oxidized derivatives. These oxidized derivatives are advantageously alcohols, aldehydes, ketones, and/or acids. In a preferred way, the oxidized compounds are for the most part alcohols.

In a preferred way, the Fischer-Tropsch fractions according to the invention are selected from among the fractions that contain more than 20% by weight of olefins that have 4 to 9 carbon atoms, of which more than 70% are linear alpha-olefins, less than 80% by weight of alkanes, and less than 10% oxidized compounds, and in a more preferred manner 5 to 8 carbon atoms.

The Pretreatment of the Feedstock

The presence in the feedstock of oxidized compounds at the level of several percent can require purification, consisting in a specific treatment, for the purpose of lowering this content to a value that is compatible with the metathesis catalyst that is used. This treatment is also to preserve the integrity of the hydrocarbon-containing composition in terms of linear alpha-olefins.

Any known treatment that is of the prior art and that corresponds to this constraint can be implemented, for example: washing cycles with water or a polar solvent, adsorption on a solid that may or may not be porous (molecular sieve, alumina, resin, etc. . . . ), selective chemical reaction. The preferred treatment is the adsorption on a molecular sieve or porous alumina.

Preparation of the Ruthenium Alkylidene Complexes Having an Unsaturated NHC-Heterocyclic Carbene.

The ruthenium alkylidene complexes can be prepared by a process for preparation comprising the following stages:

a) Forming a first reaction mixture by bringing an imidazolium salt of Formula 1S:

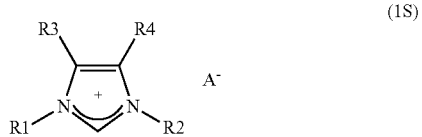

(1S)

in which
$R^1$ is an aromatic group,
$R^2$ is selected from among a cyclic secondary aliphatic alkyl group,
$R^3$ and $R^4$ are selected independently of one another from the group that consists of a hydrogen atom and an alkyl, cycloalkyl, aryl, or arylalkyl group, each being able to be substituted by alkyl, halide, or alkoxy groups or by a phenyl group that is optionally substituted by halide, alkyl, or alkoxy groups, and $A^-$ is an anion,
into contact with a strong base, in solvent, under inert atmosphere, at ambient temperature, for a period of at least 30 minutes;

b) Adding a precursor ruthenium complex to the reaction mixture that is formed in stage a) and then heating it to a temperature of at least 40° C. for a period of at least 2 hours;

c) Isolating a ruthenium alkylidene complex.

Stage b) can be carried out at a temperature of approximately 80° C., and the precursor ruthenium complex that is added to this stage can have the formula 1P:

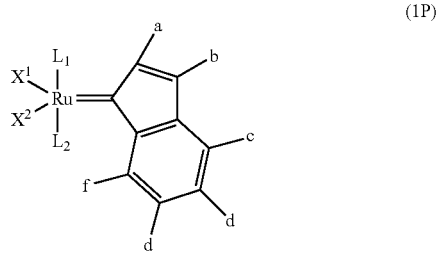

(1P)

in which
$X^1$ and $X^2$ are anionic ligands,
$L_1$ and $L_2$ are uncharged ligands, preferably of tricyclohexylphosphine, and
a, b, c, d, e, and f are selected independently of one another from the group that consists of a hydrogen atom, an alkyl group, and a heteroalkyl group.

In one embodiment, the process also comprises the following stage d):

d) Forming a second reaction mixture by bringing the ruthenium alkylidene complex that is isolated in stage c) into contact with a styrenyl ether.

Stage b) can be carried out for a period of at least 3 hours, and the precursor ruthenium complex can be of the so-called $1^{st}$-generation Hoveyda-Grubbs type.

In a preferred mode of the invention, the styrenyl ether has Formula 4H:

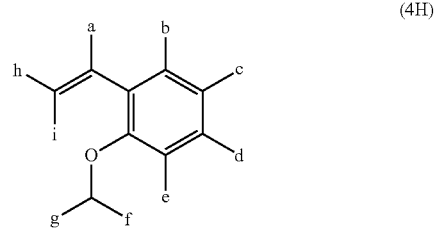

(4H)

in which a, b, c, d, e, f, g, h, and i are selected independently of one another from the group that consists of a hydrogen atom, an alkyl group, and a heteroalkyl group.

The synthesis of a ruthenium alkylidene complex comprises a preliminary stage for synthesis of a dissymmetrical imidazolium salt of Formula 1S:

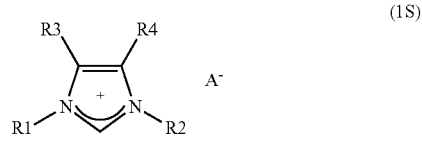

(1S)

in which
$R^1$ is an aromatic group,
$R^2$ is selected from among a cyclic secondary aliphatic alkyl group,
$R^3$ and $R^4$ are selected independently of one another from the group that consists of hydrogen and an alkyl, cycloalkyl, aryl, or arylalkyl group, each being able to be substituted by alkyl, halide or alkoxy groups, or by a phenyl group that is optionally substituted by halide, alkyl, or alkoxy groups,
and $A^-$ is an anion.

The synthesis of this salt is carried out in a single operation and comprises the following stages:

a) Forming a reaction mixture by bringing 1 equivalent (1 eq) of an aniline of Formula 2S:

(2S)

into contact with 1 equivalent (1 eq) of a compound of Formula 3S:

(3S)

in the presence of at least 4.5 equivalents (4.5 eq) of a Brønsted acid of Formula 4S:

AH (4S)

b) Forming a solution that comprises 1 equivalent (1 eq) of a dicarbonyl of Formula 5S:

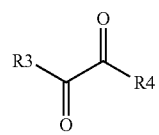

(5S)

1 equivalent (1 eq) of formaldehyde, and at least 4.5 equivalents (4.5 eq) of Brønsted acid of Formula 4, bringing said solution to at least approximately 80° C. and adding thereto the reaction mixture that is formed in stage a);

c) Leaving it to stir for at least 2 hours at at least approximately 80° C.; and d) Isolating the dissymmetrical imidazolium salt of Formula 1S.

This synthesis therefore makes it possible in a single chemical operation to obtain a 1,3-disubstituted imidazolium salt that carries an aromatic group, on the one hand, and a cycloalkyl group, on the other hand. In particular, the Brønsted acid of Formula 4S can be acetic acid. This provides an acetate-type counterion A⁻.

To make the imidazolium salt more stable, and even more reactive toward the precursor ruthenium complexes in particular, it is provided to supply a counterion A⁻ that is selected from the group of a tetrafluoroborate, hexafluorophosphate, or hexafluoroantimony anion, a tetrakis-[(3,5-trifluoromethyl)phenyl]borate anion, and a halide anion. It is therefore advantageous to provide a counterion exchange.

Use of the Catalyst

The quantity of catalytic composition used for the metathesis reaction depends on several factors such as the identity and the concentration of the reagents of the feedstock, the quantity of oxidized compounds that are present, and the reaction conditions that are employed. As a result, the necessary quantity of catalytic composition is defined in an optimal and independent manner for each reaction. However, the quantity of ruthenium complex relative to the olefins, expressed in mols, is preferably between 1 and 10,000 ppm, in a preferred manner between 1 and 200 ppm, and in a particularly preferred manner between 1 and 100 ppm.

The Process

The process for metathesis of olefins according to the invention can be carried out in the absence or in the presence of a solvent. If necessary, usable solvents according to the process of the invention can be selected from among the organic solvents, the protic solvents, or water. The solvents that can be used for metathesis according to this invention can, for example, be selected from among the aromatic hydrocarbons such as benzene, toluene, and xylenes; the halogenated aromatic hydrocarbons such as chlorobenzene and dichlorobenzene; the aliphatic hydrocarbons such as pentane, hexane, heptane and cyclohexane; the chlorinated alkanes such as dichloromethane, chloroform, and 1,2-dichloroethane; the ethers such as diethyl ether, and tetrahydrofuran; the alcohols such as methanol and ethanol, or water. A preferred solvent is chlorobenzene.

The combinations of these solvents can also be used. Any quantity of solvent can be employed, but the use of at least the minimum quantity required for dissolving the compounds of Formulas (I) and (II) is preferred, and such a minimum quantity is easily determined by one skilled in the art. The volume of the solvent can be very low relative to the volume of olefin reagents that are employed.

The process for metathesis of the olefins according to the invention is advantageously implemented while being stirred vigorously to the extent that it makes possible good contact between the reagents (some of which can be gaseous) and said catalytic composition.

The process for metathesis of the olefins according to the invention can advantageously be implemented under an atmosphere of nitrogen or argon, preferably at atmospheric pressure. Generally, a wide range of temperatures can be used.

The process for metathesis of the olefins according to the invention is advantageously implemented at a temperature of between 0° C. and 180° C., and preferably between 20° C. and 150° C., and in a more preferred manner between 20° C. and 80° C.

With the metathesis reaction leading to a minor thermal effect, the temperature is easily controlled within a narrow range.

The pressure of the reaction is advantageously between atmospheric pressure and 1 MPa, preferably between atmospheric pressure and 0.3 MPa, and in a more preferred manner between 0.1 MPa and 0.15 MPa. Low pressure is preferred for limiting the partial pressure of ethylene.

If the reagent is gaseous, it is advantageously used in pure form or in a mixture or diluted with an inert paraffin.

The process for metathesis of the olefins according to the invention is preferably conducted in a semi-open system or in a continuous system in such a way as to be able to eliminate the ethylene that is formed by the reaction system, and this is done with one or more reaction stages.

Advantageously, upon exiting the reaction system, the process according to the invention comprises a stage for neutralization of the catalyst according to the invention after the metathesis reaction. The neutralization is carried out by any means making it possible to deactivate the ruthenium complex.

The process for metathesis of the olefins according to the invention can also comprise a stage for separation of the products of the reaction, preferably by means of distillation, whereby said separation stage is advantageously implemented without a preliminary stage for separation of the neutralized ruthenium.

Actually, at the outlet of the reactor, the ruthenium that is contained in the products can be neutralized by any methods that are known to one skilled in the art. The objective of this neutralization is to deactivate the ruthenium complex to prevent it from inducing undesirable consecutive reactions that would modify the quality of the products. Usually, in addition to the neutralization stage, an additional stage for separation of the neutralized ruthenium is implemented before the stage for separation of the products, in particular by distillation. According to the process of the invention, the products of the reaction can be separated by distillation in the presence of the neutralized ruthenium compounds without harming the quality of the distilled products. The elimination of said stage makes it possible to improve the overall economy of the process.

Generally, the reaction time or the dwell time in a continuous reaction for the process for metathesis of olefins according to the invention is advantageously from approximately one second to several hours, preferably approximately five minutes to approximately 10 hours, and preferably 30 to 120 minutes. The dwell time is easily deduced from the ratio between the actual reaction volume and the output liquid volumetric flow rate; the reaction volume is defined by the liquid level controlled by a control valve.

At any time, the reaction medium consists of a liquid phase containing the products of reactions and a gaseous phase containing the ethylene that is co-produced. To promote the reaction of C5-C8 alpha-linear olefins of the feedstock toward the C8-C14 olefins, it is necessary to separate these two phases at the outlet of the reactor, preferably continuously. The liquid phase is drawn off with the level being monitored as mentioned above, while the gaseous phase (essentially consisting of C2-C6) is evacuated through a device that makes it possible to return to the reactor the reagents and products that are present (C5-C6) in the gaseous phase and to separate and to recover the by-products (C2-C4 in the case of a C5-C8 feedstock). The device is selected from among all those known to one skilled in the art that make it possible to separate a stream of C2-C6 hydrocarbons into a C2-C4 gaseous stream and a C5-C6 liquid stream, for example by a condenser followed by a flash tank.

The invention will also be further explained based on the illustrative examples provided below, which demonstrate the advantages of the catalytic compositions and of the process according to the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 13/53.830, filed Apr. 26, 2013 are incorporated by reference herein.

The examples below illustrate the invention without limiting its scope.

EXAMPLES

The Fischer-Tropsch Fraction

Denoted FT Fraction Below

The Fischer-Tropsch fraction that is used contains hydrocarbons that have 4 to 9 carbon atoms. These hydrocarbons are composed of 36% olefins and 64% alkanes (Table 1). The olefins consist of 1.5% branched olefins, 81% linear alpha-olefins, and 18% internal linear olefins. This fraction contains, in addition to hydrocarbon-containing compounds, 6.9% oxidized compounds, including a majority of alcohols (6.4%).

TABLE 1

Description of the Fischer-Tropsch Hydrocarbon-Containing Fraction Used in Examples 1 to 7

|  | % C4 | % C5 | % C6 | % C7 | % C8 | % C9 | % Total |
| --- | --- | --- | --- | --- | --- | --- | --- |
| Alkenes | 0.09 | 2.58 | 11.49 | 17.32 | 4.8 | 0.08 | 36.36 |
| Alkanes | 0.20 | 6.13 | 21.80 | 29.74 | 5.75 | 0.01 | 63.64 |

General Protocol of the Metathesis Reaction on the FT Fraction:

Approximately exactly 3,400 mg of freshly distilled FT fraction, filtered on basic alumina and degassed before the test, is injected into a reaction tube under a stream of argon. By adjusting this treatment, the quantity of oxidized compounds varies from 6% to 0.25%. The heating set-point of the tube is regulated to 50° C. When the set-point is reached, the catalyst is added in solution in a small quantity of chlorobenzene (<0.5 ml, 50 ppm of Ru, weight/charge). This corresponds to the time t=0 of the reaction. At the end of the selected reaction time, the catalyst is neutralized with several drops of butyl vinyl ether. The analysis by gas phase chromatography then makes it possible for us to determine the conversion of the olefins and to quantify the products that are formed.

Examples 1 to 6

Performance of the Catalysts 1, 2, and 3

The general protocol described above is implemented with the catalyst 1 for Examples 1-4. The catalyst 2 is used for Example 5 and the catalyst 3 for Example 6.

In Table 2, the performance of catalysts 1, 2 and 3 is defined by the conversion, expressed in terms of mols, of olefins having 6 carbon atoms (ConvC6):

Conversion C6=((mols of all of the starting C6 olefins−mols of all of the final C6 olefins)/mols of all of the starting C6 olefins)×100.

The capability of the catalyst to isomerize the double bond is expressed by %, expressed in terms of mols, of hexene-1 and heptene-1 respectively relative to all of the olefins having 6 and 7 carbon atoms, present in the products of the reaction.

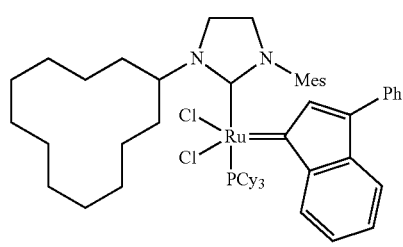

Catalyst 2

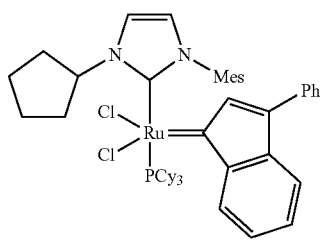

Catalyst 1

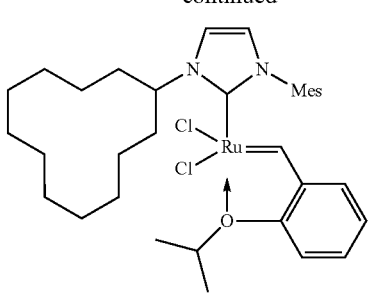

Catalyst 3

TABLE 2

Performance of Catalysts 1, 2, and 3 (Cat 1, Cat 2, and Cat 3).

| Examples | % by Weight of Alcohols in the Starting FT Feedstock | Duration of Reaction (h) | ConvC6 (mol %) | Hexene-1/TotalC6 (mol %)* | Heptene-1/TotalC7 (mol %) ** | C9 (mol %) | C10 (mol %) | C11 (mol %) | C12 (mol %) | C13 (mol %) | C14 (mol %) |
|---|---|---|---|---|---|---|---|---|---|---|---|
| Ex 1 Cat 1 | 3.8 | 3.5 | 24 | 89 | 80 | 19 | 21.4 | 27 | 21.7 | 9.3 | 1.5 |
| Ex 2 Cat 1 | 6.4 | 3.5 | 15 | 88 | 82 | 20.5 | 23.1 | 28.3 | 20.5 | 6.8 | 0.8 |
| Ex 3 Cat 1 | 0.25 | 3.5 | 57 | 92 | 78 | 11.5 | 19.1 | 29 | 25.9 | 12.2 | 2.3 |
| Ex 4 Cat 1 | 0.01 | 2 | 73 | 90 | 79 | 11.4 | 22.2 | 31.4 | 24.7 | 9.1 | 1.2 |
| Ex 5 Cat 2 | 0.2 | 4 h | 63.4 | 87 | 83 | 11.8 | 22.3 | 31.1 | 24.5 | 9.0 | 1.2 |
| Ext 6 Cat 3 | 0.1 | 4 h | 61 | 87 | 82 | 12.2 | 22.1 | 31.0 | 24.5 | 9.0 | 1.2 |

*% of Starting Feedstock = 89%
** % of Starting Feedstock = 80%

The results of Table 2 show that the catalysts 1-3 make it possible to convert the olefins of FT fractions by forming a majority of olefins having 10 to 12 carbon atoms. The level of branching of the products is the same as that of the olefins of the feedstock, i.e., less than 2%. The level of alpha-olefins in the products (measured on C6 and C7) varies very little before and after the metathesis reaction, demonstrating the low capacity of the catalysts to isomerize the double bond. The catalysts also remain selective in the presence of a large quantity of alcohols.

Example 7

Separation of the Products of the Reaction by Distillation

At the end of the reaction of Example 4 (Ex. 4), the effluent of the reaction containing ruthenium is neutralized by butyl vinyl ether, and then distilled. The ruthenium is not separated from the effluent. The temperature at the bottom of distillation is between 180° C. and 210° C. The analysis of the distilled products shows that the level of alpha-olefins determined by the number of mols of hexene-1 and heptene-1 relative to all of the olefins respectively having 6 and 7 carbon atoms has not changed before and after distillation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for metathesis of olefins from a feedstock obtained from a Fischer-Tropsch process, comprising performing said metathesis by a catalyst, which is a ruthenium alkylidene complex of Formula (I) or (II)

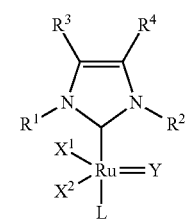

Formula I

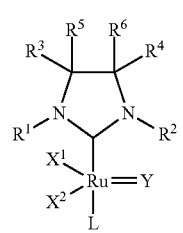

Formula II in which:
  $R^1$ is an aryl group,
  $R^2$ is a cycloalkyl group,
  $X^1$ and $X^2$, identical or different, are anionic ligands,
  L is a ligand that is an electron donor and uncharged,
  Y represents an alkylidene fragment, which may or may not be substituted, or Y forms a styrenylidene ether with L,
  $R^3$, $R^4$, $R^5$, and $R^6$—identical or different—are hydrogen, halide, alkyl, cycloalkyl, aryl or arylalkyl groups, each being able to be substituted by alkyl, halide, or alkoxy groups or by a phenyl group that is optionally substituted by halide, alkyl, or alkoxy groups,
and in which the cycloalkyl group is a cyclic secondary aliphatic alkyl.

2. The process according to claim 1, in which $R^1$ is an aromatic monocyclic or polycyclic group that has a number of carbon atoms of between 6 and 20.

3. The process according to claim 1, in which $R^2$ is a monocyclic cycloalkyl group that has a carbon number of between 3 and 24, or a polycyclic cycloalkyl group that has a carbon number of between 3 and 18.

4. The process according to claim 1, in which $R^3$, $R^4$, $R^5$, and $R^6$ can be identical or different and are selected from
a hydrogen atom,
a halide,
a linear or branched alkyl group that has 1 to 15 carbon atoms,
a monocyclic cycloalkyl group that has 3 to 10 carbon atoms, or a polycyclic cycloalkyl group that has 4 to 18 carbon atoms,
an aromatic monocyclic or bicyclic aryl group that has 6 to 20 carbon atoms,
a linear or branched arylalkyl group that carries a monocyclic aromatic cycle that has 7 to 12 carbon atoms, with the aliphatic chain comprising 1 or 2 carbon atoms.

5. The process according to claim 1, in which $X^1$ or $X^2$ is an anionic ligand selected from halides, sulfates, alkyl sulfates, aryl sulfates, alkyl sulfonates, aryl sulfonates, alkyl sulfinates, aryl sulfinates, acyls, carbonates, carboxylates, alcoholates, phenolates, amides, and pyrolides, which may or may not be substituted by one or more groups selected from alkyl groups that have 1 to 12 carbon atoms, alcoholate groups that have 1 to 12 carbon atoms, aryl groups that have 5 to 24 carbon atoms, and halides, said substituent groups, except for halides, themselves being substituted or not by one or more of the groups that are selected from halides, alkyl groups that have 1 to 6 carbon atoms, alcoholate groups that have 1 to 6 carbon atoms, and aryl groups.

6. The process according to claim 1, in which $X^1$ or $X^2$ is selected from halide ligands, benzoates, tosylates, mesylates, trifluoromethane-sulfonates, pyrolides, $CF_3CO_2$ trifluoroacetate groups, $CH_3CO_2$ acetates, alcoholates, and phenolates.

7. The process according to claim 1, in which L is a dissymmetrical, saturated or unsaturated, N-heterocyclic diaminocarbene or a phosphorated ligand of formula $PR'_3$, in which P is a phosphorus atom, and R' is selected from R and (OR), in which R are identical or different and are selected from hydrogen, halides, alkyls, cycloalkyls, aryls and aryalkyls, which may or may not be substituted, each of the groups comprising up to 20 carbon atoms, and the substituents of said groups are selected from halides, alkyl groups, and aryl groups that have up to 20 carbon atoms.

8. The process according to claim 7, in which L is a trialkylphosphine or a tricycloalkylphosphine selected from tricyclohexylphosphines, triisopropylphosphines, and tricyclopentylphosphines, a dialkylphosphine or a dicycloalkylphosphine selected from dicyclohexylphosphines, dicyclohexylphenylphosphines, di-tert-butylphosphines, and di-tert-butylchlorophosphines, or a triarylphosphine selected from triphenylphosphine, tri(methylphenyl)phosphine, trimesitylphosphine, tri(dimethylphenyl)phosphine, or tri[trifluoromethyl)phenyl]phosphine.

9. The process according to claim 8, in which $X^1$ and $X^2$ are identical and are selected from chloride or bromide ligands, L is a tricyclohexylphosphine, and Y is an indenylidene group that may or may not be substituted.

10. The process according to claim 1, in which the feedstock comprises linear olefins or linear alpha-olefins that have 3 to 10 carbon atoms.

11. The process according to claim 10, in which the feedstock also comprises branched olefins and internal olefins or alkanes or oxidized derivatives.

12. The process according to claim 1, in which the feedstock is selected from fractions that contain more than 20% by weight of olefins that have 4 to 9 carbon atoms, of which more than 70% by weight are linear alpha-olefins, less than 80% by weight of alkanes, and less than 10% oxidized compounds.

13. The process according to claim 1, in which the quantity of ruthenium complex relative to the linear alpha-olefins, expressed in terms of mols, is between 1 and 10,000 ppm.

14. The process according to claim 1, which is implemented at a temperature of between 0° C. and 180° C. and at a pressure of between atmospheric pressure and 10 MPa.

15. The process according to claim 1, which is conducted in a closed system, in a semi-open system, or in a continuous system.

16. The process according to claim 1, comprising a stage for neutralization of the catalyst after the metathesis reaction.

17. The process according to claim 16, also comprising a stage for distillation of the products of the metathesis reaction implemented without a preliminary stage for separation of the neutralized ruthenium.

18. The process according to claim 1, in which Y is an indenylidene group that may or may not be substituted.

19. The process according to claim 1, in which the ruthenium alkylidene complex is of Formula (I).

20. The process according to claim 1, in which the ruthenium alkylidene complex is of Formula (II).

21. The process according to claim 1, in which at least one of $R^3$, $R^4$, $R^5$, and $R^6$ is selected from
a halide,
a linear or branched alkyl group that has 1 to 15 carbon atoms,
a monocyclic cycloalkyl group that has 3 to 10 carbon atoms, or a polycyclic cycloalkyl group that has 4 to 18 carbon atoms,
an aromatic monocyclic or bicyclic aryl group that has 6 to 20 carbon atoms,
a linear or branched arylalkyl group that carries a monocyclic aromatic cycle that has 7 to 12 carbon atoms, with the aliphatic chain comprising 1 or 2 carbon atoms.

* * * * *